United States Patent [19]

Widmann

[11] Patent Number: 4,918,871
[45] Date of Patent: Apr. 24, 1990

[54] RENEWABLE AROMATIC CEDAR BLOCK

[76] Inventor: James C. Widmann, 8 Putnam Ave., South Norwalk, Conn. 06854

[21] Appl. No.: 347,343

[22] Filed: May 4, 1989

[51] Int. Cl.$^5$ ............................................. B24B 25/00
[52] U.S. Cl. ....................................... 51/181 R; 51/358; 51/391; 144/346; 144/347
[58] Field of Search ............. 51/181 R, 211 H, 211 R, 51/358, 407, 391, 392, 393, 204, 205 R, 205 WG; 144/346, 347; 15/1; 422/5

[56] References Cited

U.S. PATENT DOCUMENTS

| | | | |
|---|---|---|---|
| 850,889 | 4/1907 | Kelly | 144/347 X |
| 1,067,280 | 7/1913 | Smilovetz | 51/393 X |
| 1,122,350 | 12/1914 | Wysong | 144/347 X |
| 1,843,369 | 2/1932 | Olsen | 144/347 |
| 2,519,486 | 8/1950 | Lovejoy | 51/391 X |
| 3,089,294 | 5/1963 | Cowley | 51/358 X |
| 3,975,868 | 8/1976 | Botimer | 51/358 |
| 4,221,084 | 9/1980 | Frantzen | 51/181 R X |
| 4,714,644 | 12/1987 | Rich | 51/407 X |
| 4,807,404 | 2/1989 | Lewis | 51/211 R |

FOREIGN PATENT DOCUMENTS 0103560  3/1984  European Pat. Off. .......... 51/211 R Primary Examiner—Robert P. Olszewski
Assistant Examiner—Maurina Rachuba
Attorney, Agent, or Firm—Edward R. Hyde

[57] ABSTRACT

An aromatic cedar block constructed of two sections joined together for sliding contact between adjacent faces of the sections. One face having a roughed surface that scrapes into the other surface upon rubbing together to increase the cedar scent.

4 Claims, 2 Drawing Sheets

RENEWABLE AROMATIC CEDAR BLOCK

BACKGROUND OF THE INVENTION

The present invention relates to a device for producing a cedar wood scent and especially to such a device for renewing or enhancing the cedar scent from time to time.

Cedar wood not only provides a pleasing aromatic scent but is also known for repelling moths and therefore is often used for clothes closets because of its moth-repelling characteristics. Alternatively to constructing a closet of cedar wood, items made of this wood are often placed in conventional closets. For example in U.S. Pat. No. 1,741,068 there is shown a garment hanger composed of moth-repelling cedar woods upon which garments may be hung in a closet to prevent moth damaged clothes.

In addition to the moth-repelling characteristics of cedar wood, cedar objects are sometimes placed about a home simply for the pleasant aromatic scent of the wood. The scent from the wood emanates from the surface of the wood and over a period of time the scent dissipates and the cedar wood becomes less effective as a scent-producing device. In order to renew or enhance the device for scent-producing, it has been found that sanding or abrading the surface from time to time will renew it in this regard.

Accordingly it is an object of the present invention to produce a cedar wood device for producing an aromatic scent in which the scent production is renewed or enhanced.

Another object of the present invention is to produce a cedar wood device having a surface that may be conveniently abraded to enhance scent production after a time when it starts to decrease.

Another object of the invention is to provide a cedar wood scent-producing device having a pair of flat surfaces that may be rubbed together to renew and enhance the aromatic scent.

These and other objects of the invention will become apparent from the following detailed description thereof taken with the drawings.

DETAILED DESCRIPTION

Figure 1:
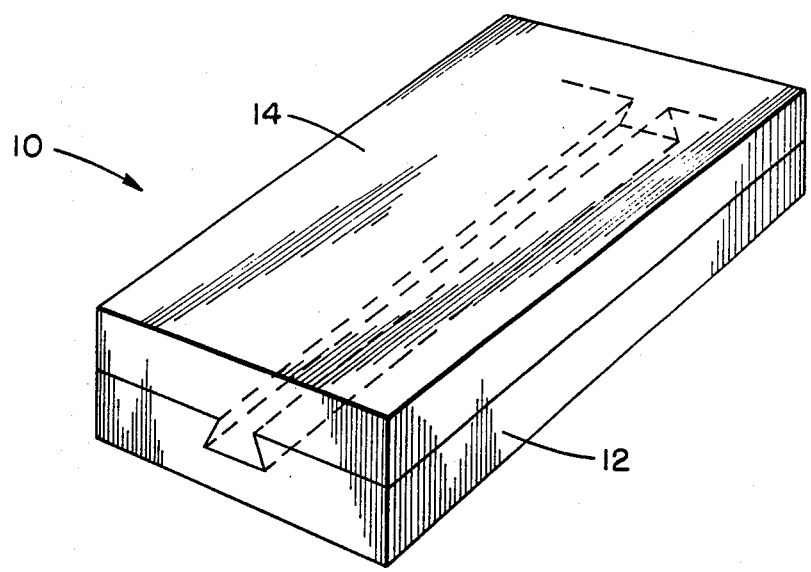
FIG. 1 is a perspective view of the cedar wood device of the present invention.

Referring now to the drawings there is shown the device 10 comprised of two rectangular blocks 12, 14 comprised of cedar wood. They are joined at the surface 16 of block 12 and surface 18 of block 14. The surface 16 has a dovetail groove or mortise 20 cut into it and correspondingly the surface 18 of block 14 has a dovetail projection or tenon 22 on it.

Figure 2:
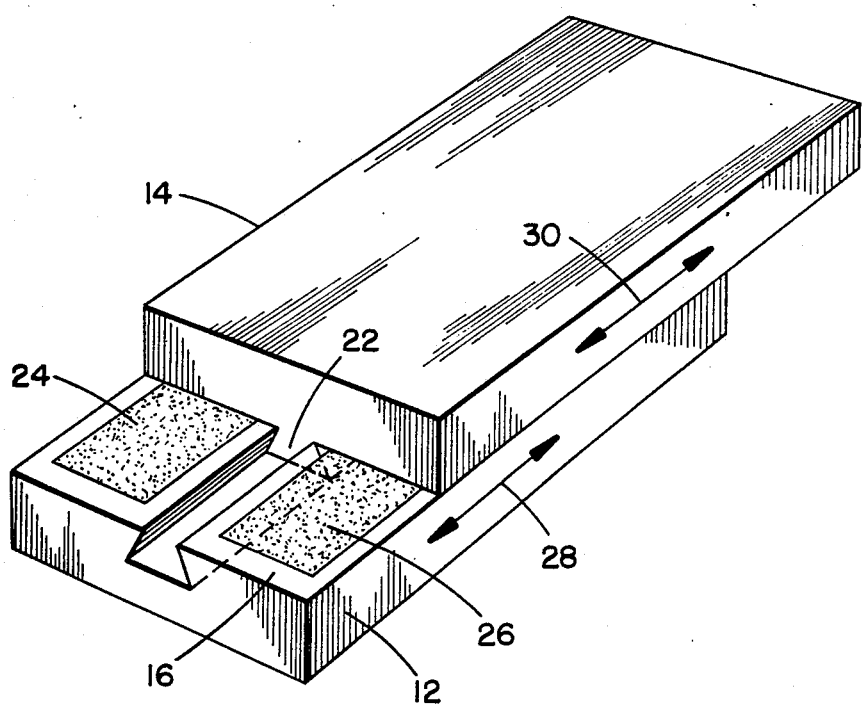
FIG. 2 is a view similar to FIG. 1 with the two blocks partially slid apart.
Figure 3:
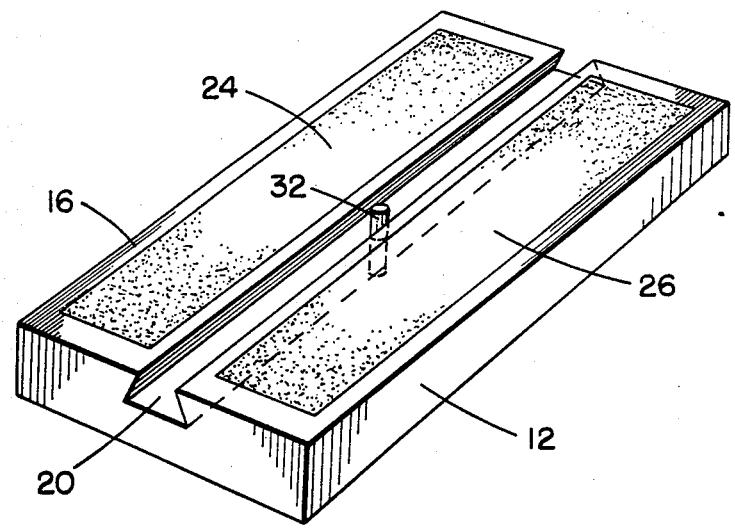
FIG. 3 is a perspective view of the device with the upper block removed.

It is seen that the dovetail joint 20, 22 permit the two blocks to be held together in a sliding relationship. In particular FIG. 2 shows block 14 partially slid out of the coinciding position exposing a portion of surface 16 of block 12. An abrading material is secured to surface 16 and may take the form of two strips of rough sandpaper 24, 26 with the roughened sanded surface presented upwardly so that it contacts surface 18 of block 14. The abrading material may take other forms as by cementing the abrading particles directly to surface 16.

It is understood then that with the two blocks in sliding position a reciprocal movement of the blocks as shown by arrows 28, 30 will result in the abrading of surface 18. This will wear away the outer surface 18 and permit the material thereunder to be exposed and this new exposure will result in a renewed or enhanced cedar scent.

Figure 4:
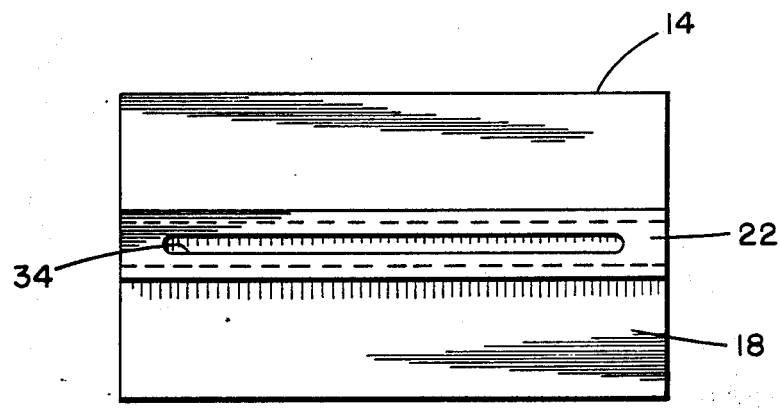
FIG. 4 is a view of the underside of the upper block.

A pin 32 is provided in the center of block 12 extending upwardly to be received in slot 34 which is cut in the underside of tenon 22. This may be fabricated by drilling a hole through block 12 in the center thereof and inserting pin 32 upwardly through the hole while the blocks are in position with the mortise within the dovetail tenon. As shown in FIG. 4 the slot 34 terminates before the ends of the block. Thus the pin 32 prevents the blocks from separating and the reciprocating motion extends slightly less than one-half the length of the block.

In use, the block is placed at any convenient location on the premises to provide a pleasing cedar wood scent. After a period of time when the scent from the surfaces of the block dissipates it may be renewed by reciprocating the blocks. This action results in the sanding of surface 18 which then emits a greater scent.

One reason that the sanding results in an increased scent is that the scent from the surface dissipates over a period of time and the sanding permits the portion under the old surface to become exposed.

Another reason is that the sanding causes roughening of the surface and, in effect, increases the surface area from which the scent emanates. A further advantage of the block design is that the blocks may be left in different stages of overlap and thus affect the amount of scent.

Although the invention has been described with respect to a specific embodiment thereof, it is understood that various embodiments and modifications may be made within the spirit and scope of the appended claims.

What is claimed is:

1. A device of cedar wood for providing an aromatic cedar scent comprising:
   a first block of cedar wood having a substantially flat surface;
   abrasive means secured to the said flat surface and being of a hardness greater than cedar wood;
   a second block of cedar wood having a substantially flat surface;
   said second block being disposed with its flat surface in contact with the abrasive means;
   means to maintain the first and second blocks in slidable contact whereby relative reciprocal sliding will abrade the said flat surface of the second block to renew the scent producing effect thereof.

2. A device as set forth in claim 1 in which said blocks are joined by a dovetail joint that permits sliding movement between the two blocks.

3. A device of cedar wood for providing an aromatic cedar scent from the surfaces thereof comprising:
   a first rectangular block of cedar wood having a substantially flat surface;
   a second rectangular block of cedar wood of substantially the same size of the first block and having a substantially flat surface;

the first and second blocks being disposed with their respective flat surfaces adjacent to each other;

the flat surface of the first block having a mortise formed therein;

the flat surface of the second block having a tenon;

said mortise and tenon forming a dovetail joint that permits relative sliding movement of the first and second cedar blocks;

two parallel strips of rough sandpaper cemented to the substantially flat surface of the first block and adapted to contact the substantially flat surface of the second block whereby relative reciprocal movement of the two blocks will cause the sandpaper strips to abrade the said substantially flat surface of the second block.

4. A device for providing an aromatic cedar scent comprising:

a first block having a substantially flat surface;

abrasive means secured to the said flat surface and being of a hardness greater than cedar wood;

a second block of cedar wood having a substantially flat surface;

said second block being disposed with its flat surface in contact with the abrasive means;

means to maintain the first and second blocks in slidable contact whereby relative reciprocal sliding will abrade the said flat surface of the second block to renew the scent producing effect thereof.

* * * * *